(12) United States Patent
Datta et al.

(10) Patent No.: US 12,144,672 B2
(45) Date of Patent: Nov. 19, 2024

(54) SYSTEM AND METHOD FOR AUTONOMOUS IDENTIFICATION OF HETEROGENEOUS PHANTOM REGIONS

(71) Applicant: GE PRECISION HEALTHCARE LLC, Wauwatosa, WI (US)

(72) Inventors: Arka Datta, Waukegan, IL (US); Krista Mae McClure, Milwaukee, WI (US); John Moore Boudry, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 234 days.

(21) Appl. No.: 17/536,323

(22) Filed: Nov. 29, 2021

(65) Prior Publication Data

US 2023/0165557 A1 Jun. 1, 2023

(51) Int. Cl.
*A61B 6/58* (2024.01)
*G06T 7/11* (2017.01)

(52) U.S. Cl.
CPC .............. *A61B 6/584* (2013.01); *G06T 7/11* (2017.01); *G06T 2207/10081* (2013.01);
(Continued)

(58) Field of Classification Search
None
See application file for complete search history.

(56) References Cited

U.S. PATENT DOCUMENTS 6,256,367 B1 * 7/2001 Vartanian ............. G01N 23/046
378/7

6,345,112 B1 * 2/2002 Summers ............... G06V 20/64
382/128

(Continued)

FOREIGN PATENT DOCUMENTS

| CN | 113423342 A | 9/2021 |
|---|---|---|
| EP | 3683771 B1 | 7/2022 |
| WO | 2017223560 A1 | 12/2017 |

OTHER PUBLICATIONS

EP application 22207648.1 filed Nov. 15, 2022—extended Search Report issued Apr. 21, 2023; 8 pages.
(Continued)

*Primary Examiner* — David P Porta
*Assistant Examiner* — Djura Malevic
(74) *Attorney, Agent, or Firm* — Fletcher Yoder P.C.

(57) ABSTRACT

A computer-implemented method includes obtaining, at a processor, a tomographic image of a phantom, wherein the phantom includes heterogeneous regions having a plurality of materials with varying attenuation coefficients. The method also includes automatically segmenting, via the processor, the heterogeneous regions from the tomographic image to generate a segmented image. The method further includes automatically identifying, via the processor, a plurality of regions of interest having varying attenuation coefficients within the tomographic image based on the segmented image. The method still further includes automatically labeling, via the processor, each region of interest of the plurality of regions of interest as representing a particular material of the plurality of materials. The method even further includes outputting, via the processor, a labeled image of the tomographic image. The method may be utilized in quality assurance testing and calibration.

20 Claims, 11 Drawing Sheets

(52) U.S. Cl.
CPC .............. *G06T 2207/20081* (2013.01); *G06T 2207/20084* (2013.01); *G06T 2207/30004* (2013.01)

(56) References Cited

U.S. PATENT DOCUMENTS

| | | | | |
|---|---|---|---|---|
| 6,404,853 | B1* | 6/2002 | Odogba | A61B 6/00 378/207 |
| 7,627,079 | B2* | 12/2009 | Boone | G01T 1/02 378/91 |
| 7,792,249 | B2* | 9/2010 | Gertner | A61N 5/1049 606/4 |
| 7,933,782 | B2* | 4/2011 | Reiner | G16H 20/10 600/300 |
| 8,018,487 | B2* | 9/2011 | Reiner | G16H 30/40 348/92 |
| 8,492,734 | B2* | 7/2013 | Yared | A61B 5/0071 382/128 |
| 8,653,480 | B2* | 2/2014 | Yared | G06T 11/003 250/458.1 |
| 8,676,302 | B2* | 3/2014 | Wang | A61B 5/0059 600/476 |
| 8,957,955 | B2* | 2/2015 | Reiner | G16H 40/40 702/81 |
| 9,082,182 | B2* | 7/2015 | Sebok | G06T 11/005 |
| 9,198,633 | B2* | 12/2015 | Freeman | A61B 6/032 |
| 9,311,722 | B2* | 4/2016 | Yared | A61B 5/0071 |
| 9,378,566 | B2* | 6/2016 | Zebaze | G06T 7/0012 |
| 9,547,893 | B2* | 1/2017 | Couch | G06T 7/337 |
| 9,566,038 | B2* | 2/2017 | Zebaze | G06T 7/70 |
| 9,861,319 | B2* | 1/2018 | Yu | A61B 5/0261 |
| 9,877,691 | B2* | 1/2018 | Zebaze | G06T 7/0012 |
| 10,022,098 | B2* | 7/2018 | Kleinszig | A61B 6/5205 |
| 10,349,912 | B2* | 7/2019 | Dorn | A61B 6/542 |
| 10,360,344 | B2* | 7/2019 | Ribbing | G16H 30/40 |
| 10,363,011 | B2* | 7/2019 | König | A61B 6/545 |
| 10,376,713 | B2* | 8/2019 | Takayanagi | A61N 5/1031 |
| 10,546,375 | B2* | 1/2020 | Couch | A61B 6/583 |
| 10,546,376 | B2* | 1/2020 | Couch | A61B 6/5229 |
| 10,922,816 | B2* | 2/2021 | Huang | G16H 30/40 |
| 10,937,206 | B2* | 3/2021 | Lu | G06T 7/11 |
| 10,939,891 | B2* | 3/2021 | Ruchala | A61B 6/032 |
| 11,000,255 | B2* | 5/2021 | Ghamari | A61B 6/583 |
| 11,051,782 | B1* | 7/2021 | Douglas | A61B 6/5217 |
| 11,253,210 | B2* | 2/2022 | Jones | G06T 7/0012 |
| 11,354,832 | B2* | 6/2022 | Bai | G06T 7/0012 |
| 11,450,096 | B2* | 9/2022 | Tan | G06N 3/045 |
| 11,532,390 | B2* | 12/2022 | Hegde | G16H 30/40 |
| 11,688,044 | B2* | 6/2023 | Delso Gafarot | G06T 7/0012 382/131 |
| 11,694,373 | B2* | 7/2023 | Akcakaya | G01R 33/4824 382/131 |
| 11,782,176 | B2* | 10/2023 | Zhan | G01N 23/046 378/207 |
| 11,794,037 | B2* | 10/2023 | Ramezanzadeh Moghadam | G16H 20/40 |
| 11,813,103 | B2* | 11/2023 | Ji | A61B 6/544 |
| 11,826,585 | B2* | 11/2023 | Ebbini | A61N 7/00 |
| 2003/0043967 | A1* | 3/2003 | Aufrichtig | A61B 6/5258 378/207 |
| 2003/0233039 | A1* | 12/2003 | Shao | A61B 6/037 600/407 |
| 2004/0058951 | A1* | 3/2004 | Lanza | A61K 49/0002 514/300 |
| 2004/0264627 | A1* | 12/2004 | Besson | A61B 6/4241 378/5 |
| 2006/0098856 | A1* | 5/2006 | Botterweck | A61B 6/032 382/131 |
| 2007/0244395 | A1* | 10/2007 | Wang | A61B 6/5247 600/476 |
| 2008/0159469 | A1* | 7/2008 | Ruhrnschopf | A61B 6/505 378/4 |
| 2010/0210931 | A1* | 8/2010 | Cuccia | A61B 5/445 600/328 |
| 2010/0272339 | A1* | 10/2010 | Feng | G06T 11/003 382/131 |
| 2011/0026791 | A1* | 2/2011 | Collins | G06F 18/00 382/131 |
| 2011/0049384 | A1* | 3/2011 | Yared | G01N 21/6456 382/128 |
| 2011/0123088 | A1* | 5/2011 | Sebok | G06T 11/005 382/197 |
| 2012/0076371 | A1* | 3/2012 | Caruba | A61B 6/037 250/252.1 |
| 2012/0106817 | A1* | 5/2012 | Shih | A61B 6/583 382/131 |
| 2012/0148131 | A1* | 6/2012 | Couch | A61B 6/542 382/131 |
| 2013/0156163 | A1* | 6/2013 | Liu | G06T 11/005 378/207 |
| 2013/0170723 | A1* | 7/2013 | Kwon | G06T 7/155 382/131 |
| 2013/0235969 | A1* | 9/2013 | Winter | A61N 5/1079 378/4 |
| 2013/0272595 | A1* | 10/2013 | Heine | G06F 17/18 702/19 |
| 2014/0003692 | A1* | 1/2014 | Yared | A61B 5/415 382/131 |
| 2014/0180082 | A1* | 6/2014 | Evans | A61B 6/502 600/436 |
| 2014/0243661 | A1* | 8/2014 | Yared | G01N 21/4795 600/425 |
| 2014/0355856 | A1* | 12/2014 | Wang | G01B 9/02083 382/131 |
| 2015/0005635 | A1* | 1/2015 | Glide-Hurst | A61B 8/15 600/442 |
| 2015/0085979 | A1* | 3/2015 | Zheng | A61B 6/583 378/207 |
| 2015/0216498 | A1* | 8/2015 | Schulze | A61B 6/584 378/207 |
| 2015/0262387 | A1* | 9/2015 | Zebaze | G06T 7/12 382/128 |
| 2016/0015356 | A1* | 1/2016 | Baiu | G09B 23/286 378/207 |
| 2016/0113612 | A1* | 4/2016 | Sedlmair | G16H 50/30 600/408 |
| 2016/0278715 | A1* | 9/2016 | Yu | G06F 30/00 |
| 2016/0287906 | A1* | 10/2016 | Nord | A61N 5/103 |
| 2016/0296188 | A1* | 10/2016 | Zebaze | A61B 6/5205 |
| 2016/0310762 | A1* | 10/2016 | Ramezanzadeh Moghadam | A61N 5/1075 |
| 2016/0370285 | A1* | 12/2016 | Jang | C08J 3/005 |
| 2017/0112457 | A1* | 4/2017 | Allinson | A61B 6/4258 |
| 2017/0119333 | A1* | 5/2017 | Zebaze | G06T 7/0012 |
| 2017/0164835 | A1* | 6/2017 | Wiest | A61B 6/5207 |
| 2017/0245825 | A1* | 8/2017 | Star-Lack | A61B 6/5217 |
| 2018/0014806 | A1* | 1/2018 | Lu | A61B 6/032 |
| 2018/0028133 | A1* | 2/2018 | Jones | G06T 5/20 |
| 2018/0061058 | A1* | 3/2018 | Xu | G06N 3/084 |
| 2018/0116620 | A1* | 5/2018 | Chen | G06T 7/136 |
| 2018/0140272 | A1* | 5/2018 | Ruchala | A61B 6/545 |
| 2018/0224592 | A1* | 8/2018 | Holdsworth | G06T 7/001 |
| 2018/0247450 | A1* | 8/2018 | Varfolomeev | G06T 17/10 |
| 2018/0289336 | A1 | 10/2018 | Osawa | |
| 2018/0330233 | A1* | 11/2018 | Rui | G06N 3/045 |
| 2019/0046813 | A1* | 2/2019 | Zhou | A61N 5/10 |
| 2019/0054194 | A1* | 2/2019 | Yu | G06T 7/168 |
| 2019/0108441 | A1* | 4/2019 | Thibault | G01N 23/046 |
| 2019/0251694 | A1 | 8/2019 | Han | |
| 2019/0266436 | A1* | 8/2019 | Prakash | A61B 6/586 |
| 2019/0325621 | A1* | 10/2019 | Wang | G06N 3/045 |
| 2019/0388054 | A1* | 12/2019 | Qiu | G09B 23/286 |
| 2020/0065969 | A1* | 2/2020 | Huang | G06V 10/82 |
| 2020/0085404 | A1* | 3/2020 | Siewerdsen | G06T 7/60 |
| 2020/0170612 | A1* | 6/2020 | Browne | G09B 23/286 |
| 2020/0211710 | A1* | 7/2020 | Do | G16H 50/30 |
| 2020/0234471 | A1* | 7/2020 | Lu | G06T 11/005 |
| 2020/0237319 | A1* | 7/2020 | Yi | G06T 7/0012 |
| 2020/0359911 | A1* | 11/2020 | Olender | A61B 5/1076 |
| 2021/0236080 | A1 | 8/2021 | Herrmann | |
| 2021/0239775 | A1* | 8/2021 | Gallippi | G01R 33/24 |

(56) References Cited

U.S. PATENT DOCUMENTS

| | | | |
|---|---|---|---|
| 2021/0239862 A1* | 8/2021 | Petrak | G01T 1/2907 |
| 2022/0245928 A1* | 8/2022 | Tan | G06N 3/045 |
| 2022/0322940 A1* | 10/2022 | Trakic | A61B 5/05 |
| 2022/0342098 A1* | 10/2022 | Zhan | A61B 6/032 |
| 2023/0320688 A1* | 10/2023 | Datta | G06T 7/0002 |
| | | | 378/207 |

OTHER PUBLICATIONS

CN113423342—English Abstract, Espacenet search results Feb. 19, 2024; 1 page.

JP application 2022-175193 filed Nov. 1, 2022—Office Action issued Nov. 22, 2023; Machine Translation, 8 pages.

* cited by examiner

Rod position and index (X co-ordinate || Y co-ordinate || rod index || rod description)

| | | | |
|---|---|---|---|
| "135.6249" | "269.8059" | "R1" | "ROI_Left_Solid Water" |
| "157.9808" | "190.2792" | "R2" | "ROI_5mg" |
| "177.6965" | "345.9367" | "R3" | "ROI_20mg" |
| "230.4832" | "147.9201" | "R4" | "ROI_CB_230" |
| "245.1848" | "256.8452" | "R5" | "ROI_Brain" |
| "253.0689" | "309.321" | "R6" | "ROI_Liquid Water" |
| "258.7393" | "367.006" | "R7" | "ROI_Liquid Water" |
| "311.577" | "170.769" | "R8" | "ROI_10mg" |
| "332.4694" | "325.2548" | "R9" | "ROI_15mg" |
| "353.9494" | "241.5581" | "R10" | "ROI_Right_Solid Water" |

SYSTEM AND METHOD FOR AUTONOMOUS IDENTIFICATION OF HETEROGENEOUS PHANTOM REGIONS

BACKGROUND

The subject matter disclosed herein relates to systems and methods for deep-learning based autonomous identification of heterogeneous phantom regions.

Volumetric medical imaging technologies use a variety of techniques to gather three-dimensional information about the body. For example, computed tomography (CT) imaging system measures the attenuation of X-ray beams passed through a patient from numerous angles. Based upon these measurements, a computer is able to reconstruct images of the portions of a patient's body responsible for the radiation attenuation. As will be appreciated by those skilled in the art, these images are based upon separate examination of a series of angularly displaced measurements. It should be pointed out that a CT system produces data that represent the distribution of linear attenuation coefficients of the scanned object. The data are then reconstructed to produce an image that is typically displayed on a screen, and may be printed or reproduced on film.

Phantoms are commonly utilized in the CT system during the calibration process and for quality assurance (QA) testing. For a homogeneous phantom (e.g., constructed using a single material where the attenuation coefficient doesn't change within the phantom cross section), it is easy to identify a region within such a phantom. A heterogeneous phantom (e.g., constructed using multiple materials where the attenuation coefficient changes within a phantom image depending on the material) is widely used in QA of a single energy and dual energy CT scanner for determining and conforming various image quality parameter metrics. Currently, manual intervention is required to identify the regions of interest (ROIs) for different materials as an intermediate step of the QA testing. In addition, a heterogeneous phantom can be advantageous for calibration purposes in multi-energy photon counting CT scanners. Thus, correct and autonomous identification of a heterogeneous phantom ROIs is needed to execute such tasks.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a computer-implemented method is provided. The method includes obtaining, at a processor, a tomographic image of a phantom, wherein the phantom includes heterogeneous regions having a plurality of materials with varying attenuation coefficients. The method also includes automatically segmenting, via the processor, the heterogeneous regions from the tomographic image to generate a segmented image. The method further includes automatically identifying, via the processor, a plurality of regions of interest having varying attenuation coefficients within the tomographic image based on the segmented image. The method still further includes automatically labeling, via the processor, each region of interest of the plurality of regions of interest as representing a particular material of the plurality of materials. The method even further includes outputting, via the processor, a labeled image of the tomographic image.

In one embodiment, a computer-implemented method is provided. The method includes beginning, via a processor, a calibration of a tomographic imaging system. The method also includes obtaining, via the processor, a tomographic image of a phantom utilizing the tomographic imaging system, wherein the phantom includes heterogeneous regions having a plurality of materials with varying attenuation coefficients. The method also includes automatically segmenting, via the processor, the heterogeneous regions from the tomographic image to generate a segmented image. The method further includes automatically identifying, via the processor, a plurality of regions of interest having varying attenuation coefficients within the tomographic image based on the segmented image. The method still further includes automatically labeling, via the processor, each region of interest of the plurality of regions of interest as representing a particular material of the plurality of materials. The method further includes calculating, via the processor, a respective calibration vector for one or more regions of interest of the plurality of regions of interest based on the labeling of each region of interest.

In one embodiment, a computer-implemented method is provided. The method includes beginning, via a processor, quality assurance testing of a tomographic imaging system. The method includes obtaining, via the processor, a tomographic image of a phantom utilizing the tomographic imaging system, wherein the phantom includes heterogeneous regions having a plurality of materials with varying attenuation coefficients. The method also includes automatically segmenting, via the processor, the heterogeneous regions from the tomographic image to generate a segmented image. The method further includes automatically identifying, via the processor, a plurality of regions of interest having varying attenuation coefficients within the tomographic image based on the segmented image. The method still further includes automatically labeling, via the processor, each region of interest of the plurality of regions of interest as representing a particular material of the plurality of materials. The method even further includes calculating, via the processor, image quality metrics based on the labeling of each region of interest.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 6 is example of a chart including coordinates, index, and material description, in accordance with aspects of the present disclosure;

DETAILED DESCRIPTION

Figure 1:
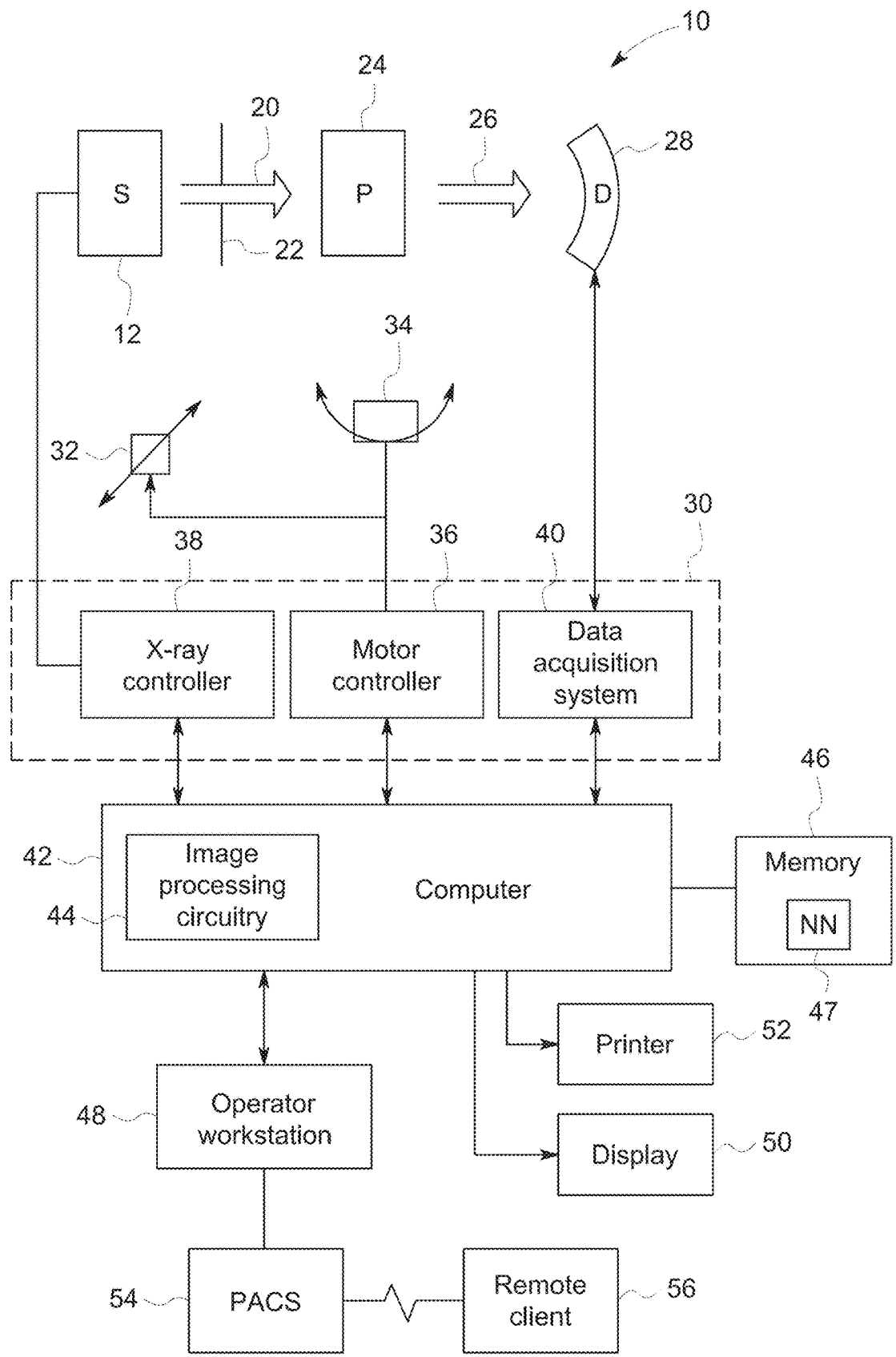
FIG. 1 is a schematic illustration of an embodiment of a computed tomography (CT) system configured to acquire CT images of a patient and process the images, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

Deep-learning (DL) approaches discussed herein may be based on artificial neural networks, and may therefore encompass one or more of deep neural networks, fully connected networks, convolutional neural networks (CNNs), perceptrons, encoders-decoders, recurrent networks, wavelet filter banks, u-nets, generative adversarial networks (GANs), or other neural network architectures. The neural networks may include shortcuts, activations, batch-normalization layers, and/or other features. These techniques are referred to herein as deep-learning techniques, though this terminology may also be used specifically in reference to the use of deep neural networks, which is a neural network having a plurality of layers.

As discussed herein, deep-learning techniques (which may also be known as deep machine learning, hierarchical learning, or deep structured learning) are a branch of machine learning techniques that employ mathematical representations of data and artificial neural networks for learning and processing such representations. By way of example, deep-learning approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for deep-learning based autonomous identification of heterogeneous phantom regions (e.g., via region of interest location algorithm). The disclosed embodiments include obtaining or acquiring (e.g., via a CT scanner) a tomographic image of a phantom. The phantom includes heterogeneous regions having a plurality of materials (e.g., within rods) with varying or different attenuation coefficients. The disclosed embodiments also include automatically segmenting (e.g., via a trained deep neural network) the heterogeneous regions from the tomographic image to generate a segmented image (e.g., segmentation mask). The disclosed embodiments further include automatically identifying a plurality of regions of interest having varying attenuation coefficients within the tomographic image based on the segmented image. In particular, the disclosed embodiments include automatically determining an angle of rotation of the phantom relative to a properly positioned phantom (via comparison of the segmentation mask to a reference image (e.g., reference or template segmentation mask serving as a ground truth) for a properly positioned phantom). The disclosed embodiments yet further include automatically labeling each region of interest of the plurality of regions of interest as representing a particular material of the plurality of materials. The disclosed embodiments still further include outputting a labeled or annotated image of the tomographic image with the labeled regions of interest. In certain embodiments, a rotational angle of the phantom within the tomographic image and/or a chart having both at least a label and the particular material for each region of interest. The disclosed embodiments enable the use of a multi-structure in the calibration and QA process without modifying any phantom hardware (e.g., adding a tracer/marker to identify regions). In addition, the deep neural network can be trained with any phantom at any scanning protocols. The ability to automatically identify the regions of interest within the heterogeneous phantom eliminates the need for manual intervention while ensuring the efficacy of the region identification.

With the foregoing discussion in mind. FIG. 1 illustrates an embodiment of an imaging system 10 for acquiring and processing image data in accordance with aspects of the present disclosure. Although the following embodiments are discussed in terms of the computed tomography (CT) imaging system, the embodiments may also be utilized with other imaging systems (e.g., X-ray, PET, CT/PET, SPECT, nuclear CT, magnetic resonance imaging, etc.). In the illustrated embodiment, system 10 is a CT system designed to acquire X-ray projection data, to reconstruct the projection data into a tomographic image, and to process the image data for display and analysis. The CT imaging system 10 includes an X-ray source 12. As discussed in detail herein, the source 12 may include one or more X-ray sources, such as an X-ray tube or solid-state emission structures. The X-ray source 12, in accordance with present embodiments, is configured to emit an X-ray beam 20 at one or more energies.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets or reconstructed images.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein. The memory 46 also stores one or more algorithms and/or neural networks 47 that may be utilized in autonomous identification of heterogeneous phantom regions as described in greater detail below.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, to observe reconstructed images, to control imaging, and so forth. Additionally, the system 10 may include a printer 52 coupled to the operator workstation 48 and configured to print images. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Further, the computer 42 and operator workstation 48 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

While the preceding discussion has treated the various exemplary components of the imaging system 10 separately, these various components may be provided within a common platform or in interconnected platforms. For example, the computer 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 30 may be provided as part of such a computer or workstation or as part of a separate system dedicated to image acquisition.

Figure 2:
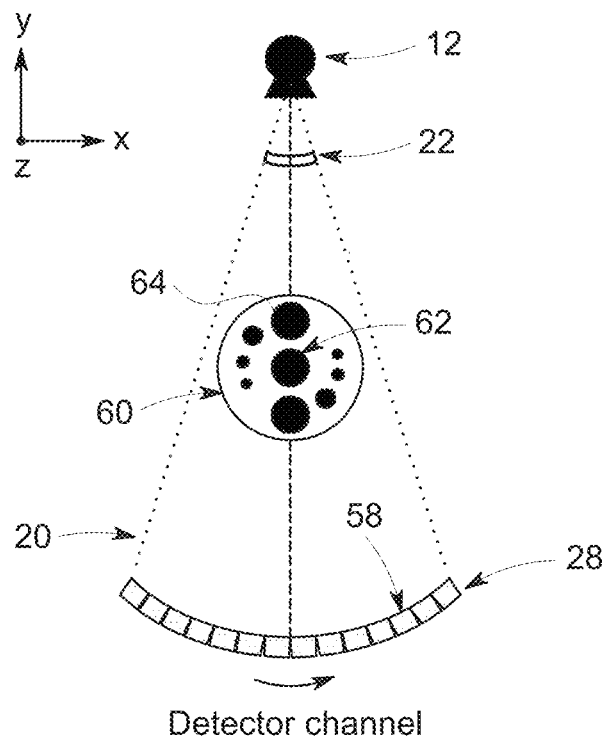
FIG. 2 is a schematic view of an X-ray source and a multi-row X-ray detector (e.g., as viewed in an X-Y plane) imaging a heterogeneous phantom, in accordance with aspects of the present disclosure.
Figure 3:
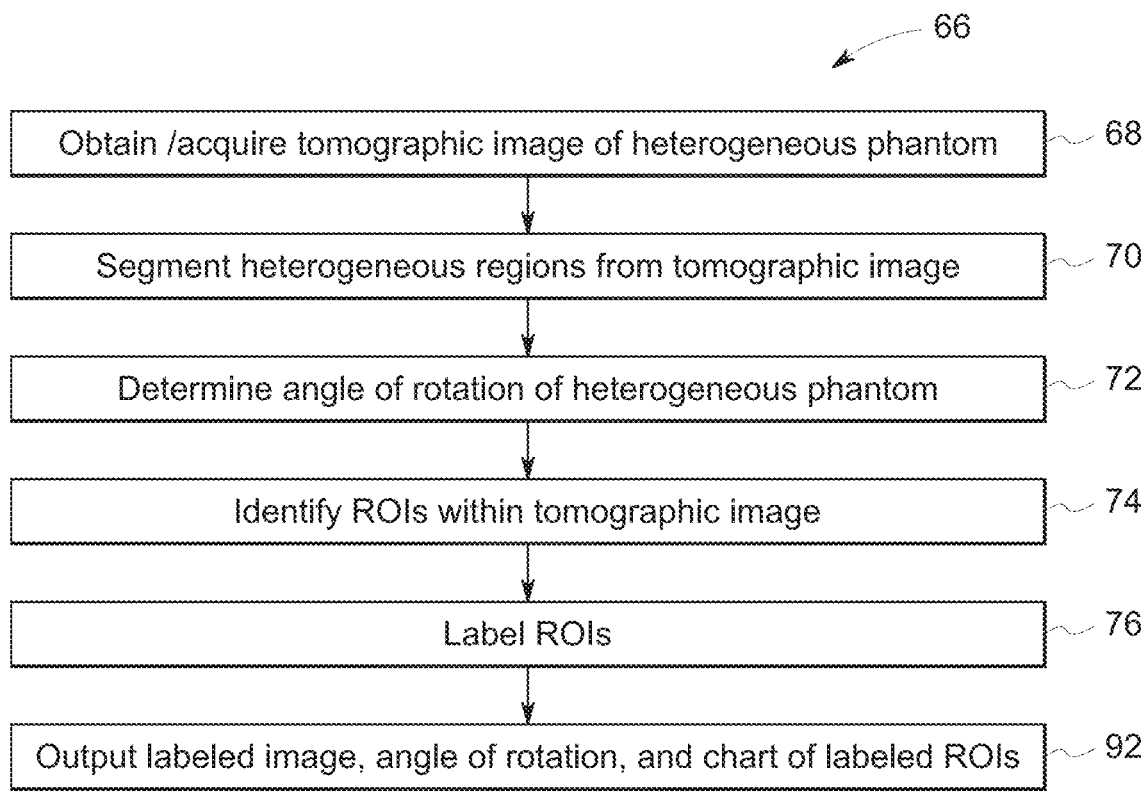
FIG. 3 is a flow chart of a method for identifying regions within a heterogeneous phantom, in accordance with aspects of the present disclosure.

With the preceding discussion of an overall imaging system 10 in mind, and turning to FIG. 2, an example of the X-ray source 12 and the detector 28 (e.g., having a plurality of rows 58) are illustrated in an X-Y plane. As depicted, the collimator 22 is disposed between the X-ray source 12 and the detector 28 and determines the shape of the X-ray beam 20. A heterogeneous phantom 60 is disposed between the X-ray source 12 and the detector 28 and may be utilized in a calibration process as well as QA testing of a CT imaging system (e.g., system 10 in FIG. 1) as described below. The heterogeneous phantom 60 includes heterogeneous regions 62 having a plurality of materials with varying or different attenuation coefficients. In particular, each heterogeneous region 62 may be a rod 64 made of a different material with a different attenuation coefficient. Some of the rods may have the same material. Some of the rods may have the same material but at different concentrations. Examples of the material may be calcium, iodine, adipose tissue, water, iron, tissue mimicking materials (e.g., brain, adipose tissue, etc.), and blood mimicking materials As described herein, techniques (e.g., a region of interest location algorithm) may be utilized for the automatically identifying the regions (e.g., rods) of varying or different attenuation coefficients within the heterogeneous phantom. In particular, the techniques utilize a holistic approach combining system hardware and a deep learning-based model to identify these regions within the heterogeneous phantom. FIG. 3 is a flow chart of a method 66 for identifying regions within a heterogeneous phantom. One or more steps of the method 66 may be performed by one or more components (e.g., processing circuitry) of the CT imaging system in FIG. 1 or a device separate or remote from the CT imaging system.

The method 66 includes obtaining or acquiring a tomographic image of a heterogeneous phantom (block 68). The tomographic image may be obtained utilizing a predefined protocol (e.g., kV, mA, bowtie, rotation speed, aperture, etc.).

The method 66 also includes automatically segmenting heterogeneous regions (e.g., having a plurality of materials with varying or different attenuation coefficients) from the tomographic image to generate a segmented image (e.g., segmentation mask) (block 70). A trained deep neural network may be utilized for performing segmentation of the heterogeneous regions. In certain embodiments, alternative techniques (e.g., if, then statements) may be utilized in performing the segmentation of the heterogeneous regions.

The method 66 further includes automatically determining an angle of rotation (e.g., angular rotation) of the heterogeneous phantom relative to a properly positioned heterogeneous phantom (or the heterogeneous phantom at a predefined position) (block 72). Determining the angle of rotation includes comparing the segmentation image derived from the tomographic image to a reference image of a properly positioned heterogeneous phantom. The reference image may be a segmentation image or segmentation mask derived from a tomographic image of the properly positioned heterogeneous phantom. A similarity index may be utilized to determine the angle of rotation based on the comparison between the segmentation image and the reference image. There is no limit on the angle of rotation of the phantom that can be determined.

The method 66 still further includes automatically identifying a plurality of ROIs having varying attenuation coefficients within the tomographic image based on the segmented image (i.e., based on the determined angle of rotation) (block 74). The plurality of ROIs correspond to the heterogeneous regions within the heterogeneous phantom. Identifying the ROIs includes identifying multi-connectivity (e.g., 8) pixel regions within the tomographic image. Identifying the ROIs also includes identifying pixels regions greater than a predefined number (e.g., 100) of connected pixels.

Figure 4:
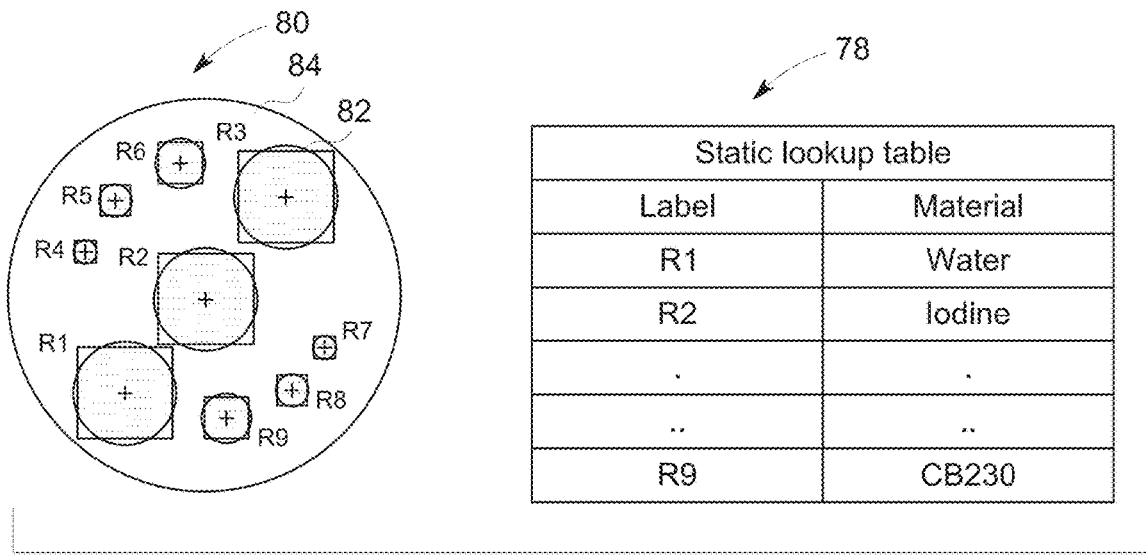
FIG. 4 is an example of a static lookup table and labeled or annotated tomographic image, in accordance with aspects of the present disclosure.
Figure 5:
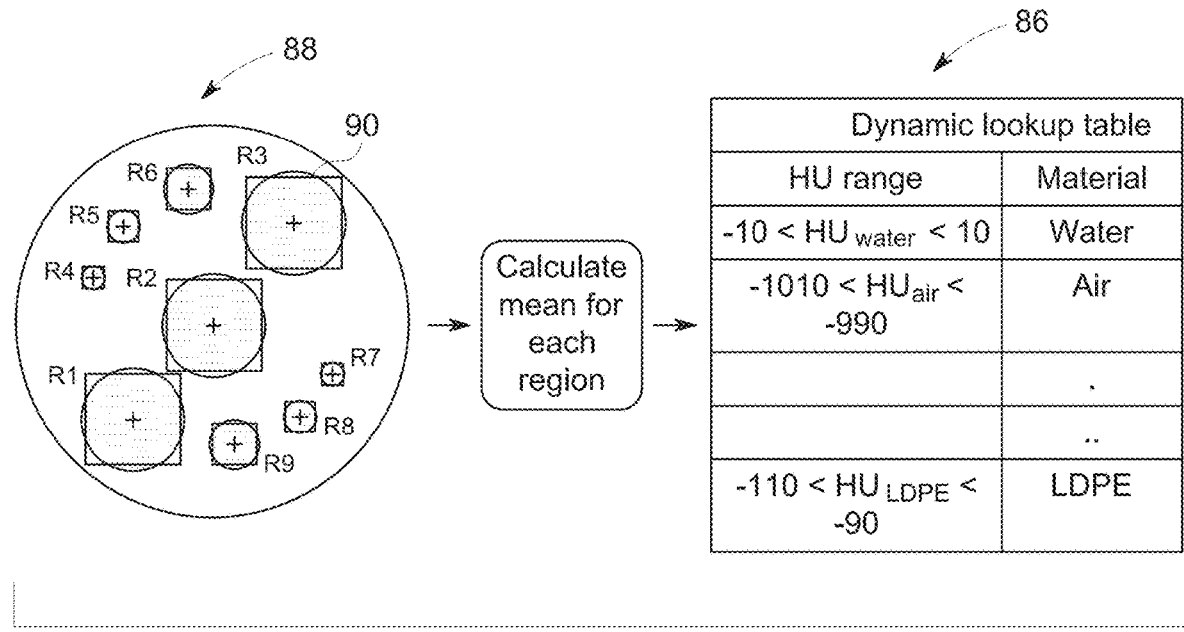
FIG. 5 is an example of a dynamic lookup table and labeled or annotated tomographic image, in accordance with aspects of the present disclosure.

The method 66 yet further includes automatically labeling each ROI of the plurality of ROIs as representing a particular material of the materials with the varying or different attenuation coefficients (block 76). In certain embodiments, labeling the ROIs includes generating a label matrix for the plurality of ROIs and comparing the label matrix to a static lookup table to label/identify each ROI as representing a particular material. FIG. 4 is an example of a static lookup table 78 and labeled or annotated tomographic image 80. In FIG. 4, in the labeled image 80, each ROI 82 is associated with a label 84 (e.g., R1, R2, R3, etc.) of the label matrix. In static lookup table 78 in FIG. 4, each label 84 corresponds to a specific material. In certain embodiments, labeling the ROIs includes calculating a mean CT number (e.g., in Hounsfield units (HU)) for each ROI and comparing the respective CT number to a dynamic lookup table to determine the material. The dynamic lookup table associates specific CT number ranges with specific materials. FIG. 5 is an example of a dynamic lookup table 78 and labeled or annotated tomographic image 88. In FIG. 5, a mean CT number is determined for each ROI 90. In the dynamic lookup tale 86 in FIG. 5, each material is associated within a particular CT number range (e.g., HU range).

Returning to FIG. 3, the method 66 even further includes outputting a labeled or annotated image of the tomographic image (e.g., labeled tomographic images 80, 88 in FIGS. 4, 5) (block 92). In certain embodiments, the angle of rotation of the heterogeneous phantom is also outputted. In certain embodiments, a chart is also outputted that includes at least a label and a particular material (or concentration or density) of the material) for each ROI in the labeled image. The chart may also in include coordinates for each ROI. An example of a chart 94 that may be outputted is provided in FIG. 6.

Figure 7:
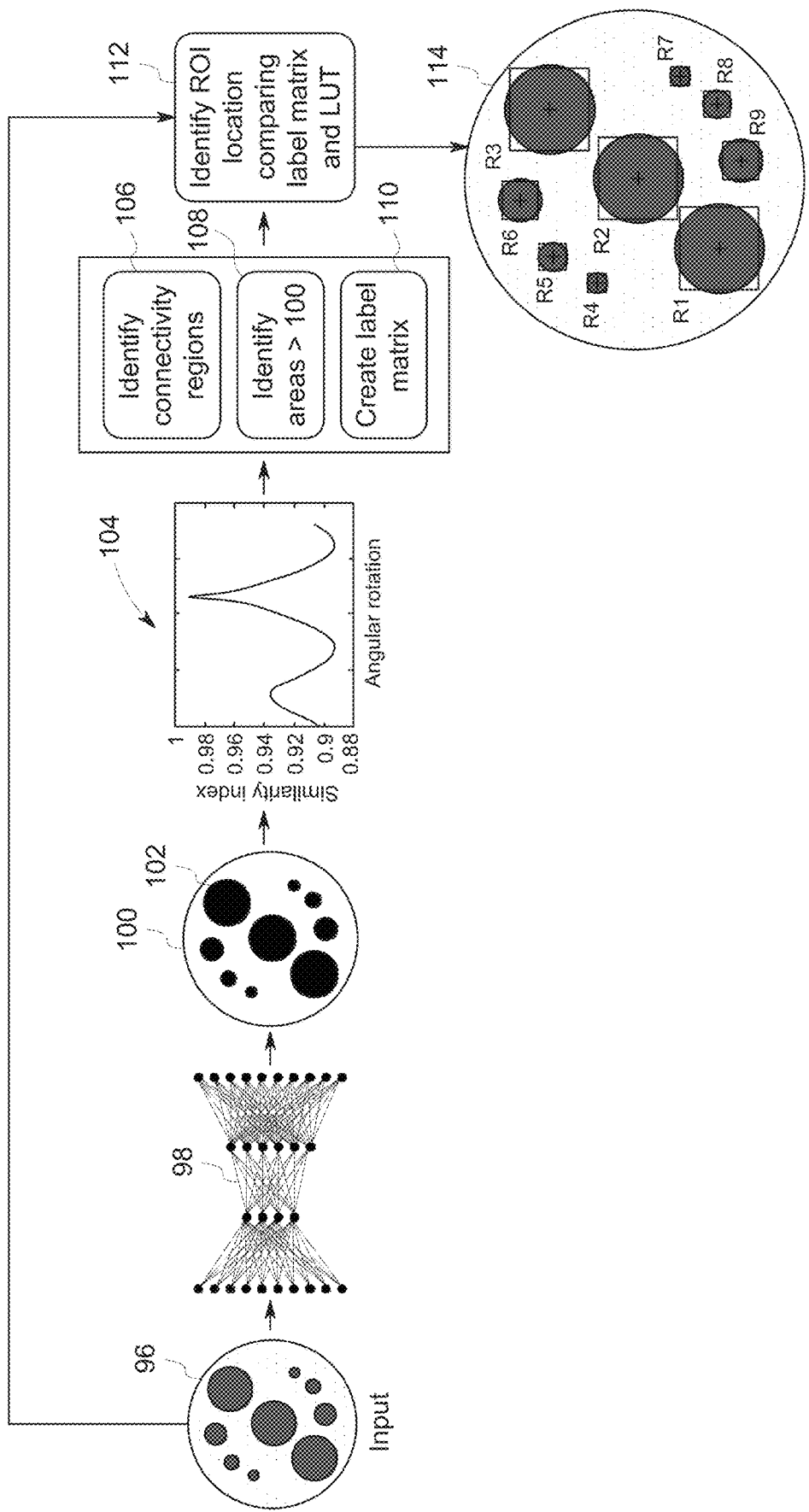
FIG. 7 is schematic diagram of the method in FIG. 3, in accordance with aspects of the present disclosure.

FIG. 7 is schematic diagram of the method 66 (e.g., ROI location algorithm) in FIG. 3. As depicted in FIG. 3, an image 96 (e.g., unlabeled tomographic image) of a heterogeneous phantom is inputted into a trained deep neural network 98 (e.g., trained convolutional neural network). The trained deep neural network 98 generates a segmented image 100 (e.g., segmentation mask) from the image 96 having heterogeneous regions 102 having a plurality of materials with varying or different attenuation coefficients. The segmented image 100 is compared to a reference or template image from which a similarity index 104 may be used to determine an angle of rotation for the heterogeneous phantom in the image 96 relative to a properly positioned heterogeneous phantom (or heterogeneous phantom at a predefined position). Regions of interest are identified in the image 96 by identifying connectivity regions (as indicated by reference numeral 106) and pixel regions of greater than 100 pixels (as indicated by reference numeral 108). In addition, a label matrix is created for the regions of interest in the image 96 (as indicated by reference numeral 110). The regions of interest in the image 96 may be identified/labeled by comparing the label matrix and a lookup table (as indicated by reference numeral 112). A labeled or annotated image 114 of the image 96 is outputted. All of the steps of the depicted method may be automated.

Figure 8:
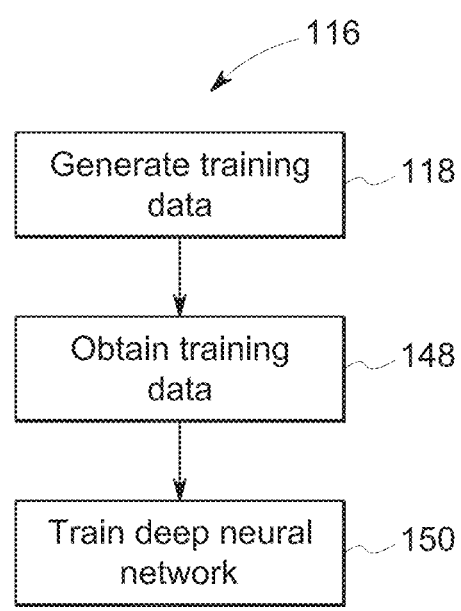
FIG. 8 is a flow chart of a method for training a deep neural network for identifying regions within a heterogeneous phantom, in accordance with aspects of the present disclosure.

FIG. 8 is a flow chart of a method 116 for training a deep neural network (e.g., deep neural network 98 in FIG. 7) for identifying regions within a heterogeneous phantom. One or more steps of the method 116 may be performed by one or more components (e.g., processing circuitry) of the CT imaging system in FIG. 1 or a device separate or remote from the CT imaging system.

Figure 9:
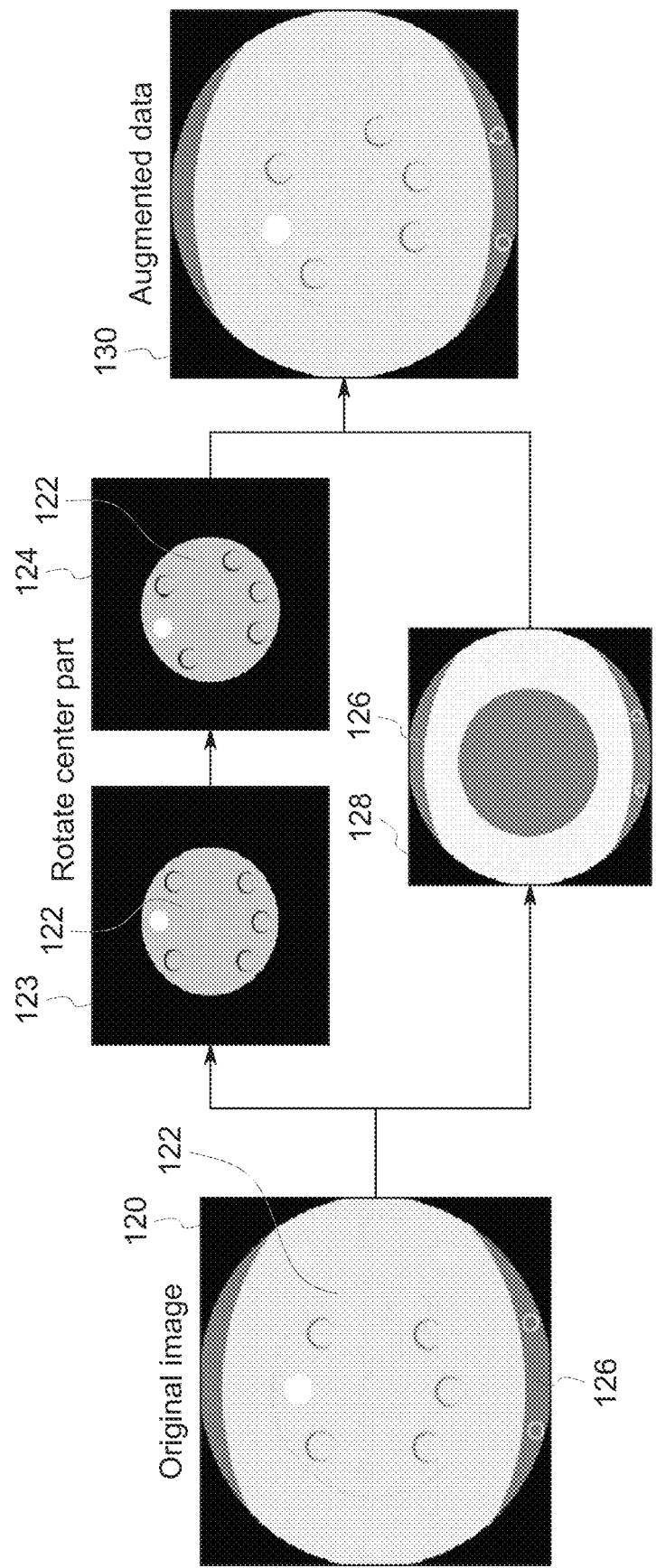
FIG. 9 is schematic diagram for generating training data from an unaugmented image, in accordance with aspects of the present disclosure.

The method 116 includes generating training data for the deep neural network (e.g., convolutional neural network) (block 118). As depicted in FIG. 9, the initial training data may be generated by taking an unaugmented image 120 (e.g., tomographic image) of a heterogeneous phantom and randomly rotating a central portion 122 of the image 120 (as indicated in images 123, 124) while keeping a peripheral part 126 of the image 120 (as indicated in image 128) intact to generate an augmented image or data 130 that includes central portion 122 rotated relative to the image 120. A number of augmented images 130 may be generated from the image 120 with different degrees of rotation of the central portion 122. These augmented images may be manually processed to generate a label (e.g., segmentation image or segmentation mask) for the heterogeneous regions in each augmented image. Thus, image-label pairs (including the augmented image and the segmentation image) may be generated from the augmented images.

Figure 10:
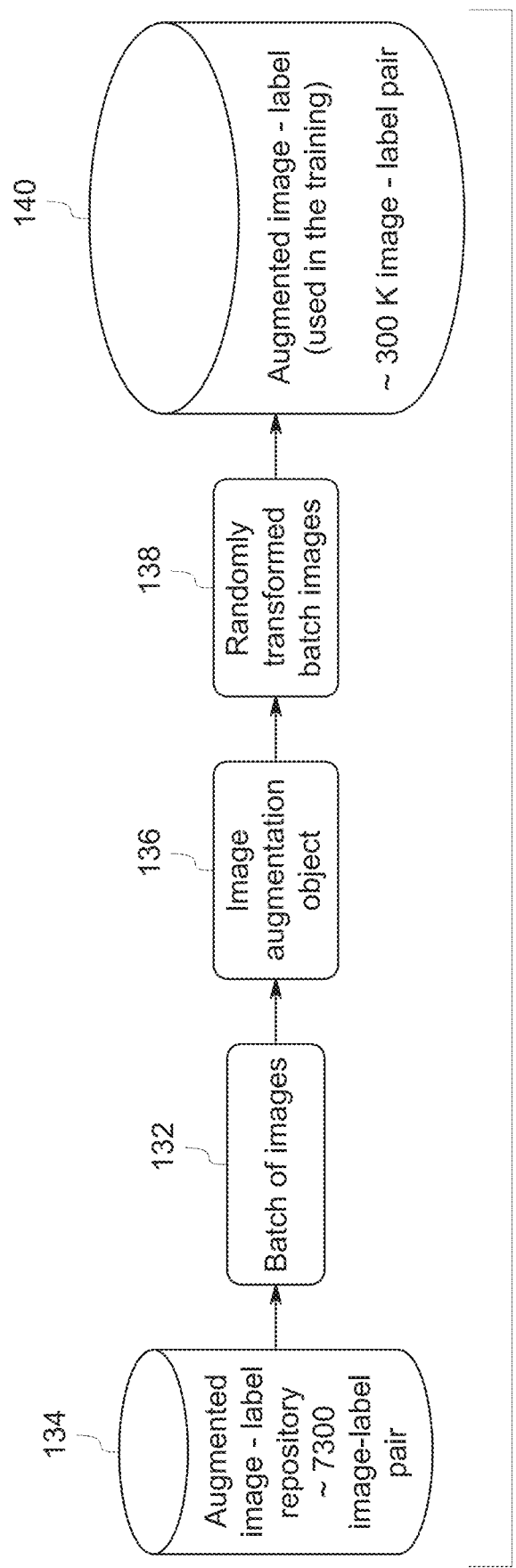
FIG. 10 is a schematic diagram for generating further training data, in accordance with aspects of the present disclosure.
Figure 11:
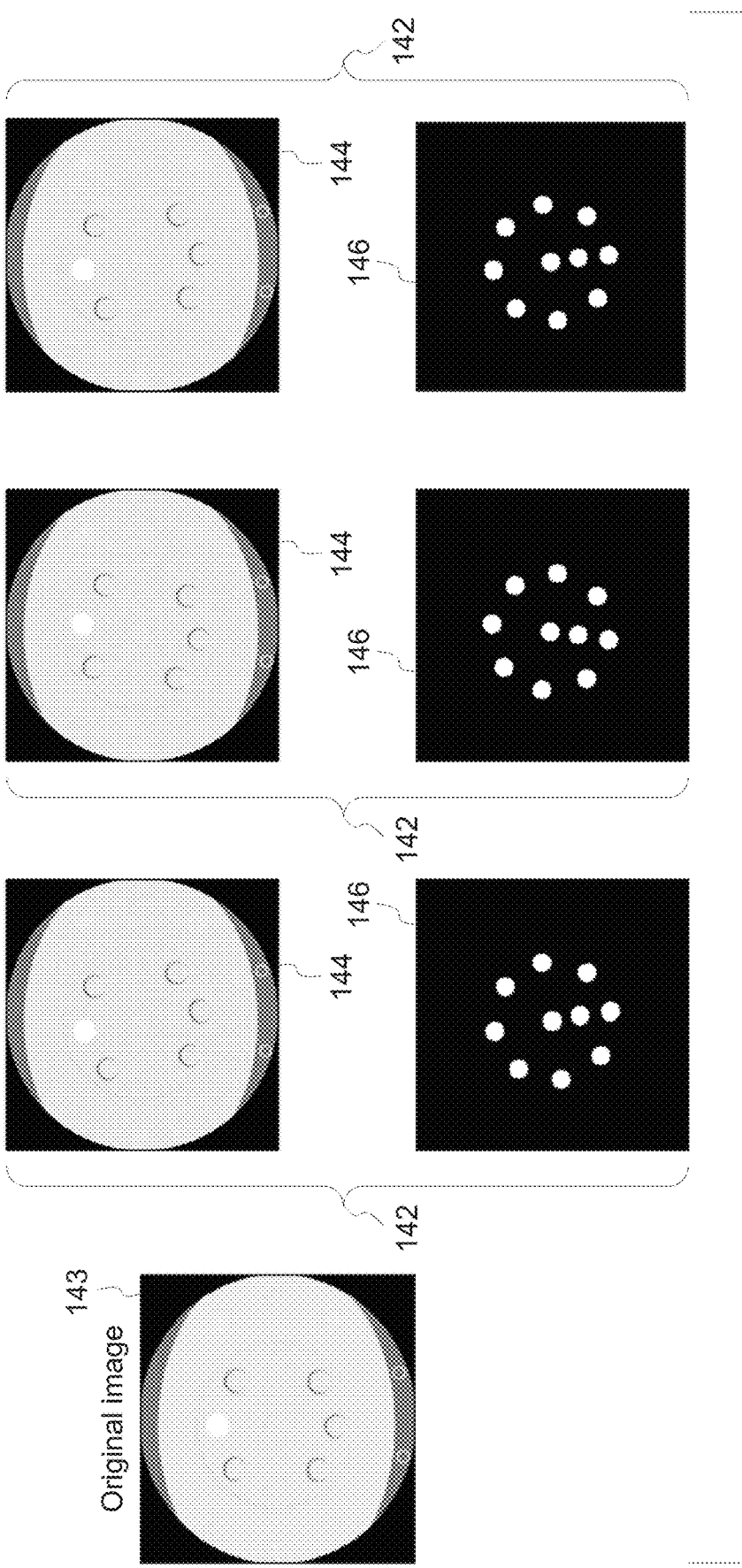
FIG. 11 are examples of training data of image-label pairs generated from an unaugmented image, in accordance with aspects of the present disclosure.

From these image-label pairs, further training data (different from the original training data) may be generated while the deep neural network (e.g., convolutional neural network) is being trained. For example, in-place data augmentation or on-the-fly data augmentation (e.g. utilizing ImageDataGenerator class of Keras deep learning network library) may be utilized to generate the additional training data. As depicted in FIG. 10, a batch of images 132 is obtained from a repository 134 of the augmented image-label pairs and data augmentation is performed (as indicated by reference numeral 136) to generate randomly transformed batch images 138 which are provided to form a larger training dataset 140 (augmented image-label pairs) for training the deep neural network. Data augmentation may include random translations and rotations, horizontal flips, vertical flips, width shifts, and height shifts. In addition, noise (e.g., Gaussian noise) may be introduced into the images. FIG. 11 provides different examples of augmented image-label pairs 142 obtained from an unaugmented image 143. Each augmented image-label pair 142 in FIG. 11 includes an augmented image 144 and a segmentation image 146 (e.g., segmentation mask for the heterogeneous regions).

Returning to FIG. 8, the method 116 also includes obtaining the training data (e.g., image-label pairs) (block 148). The method 116 further includes training the deep neural network to generate a trained deep neural network (block 150) that can segment the heterogeneous regions from an inputted image of a heterogeneous phantom. It should be noted that may be trained for any scanning protocol.

Figure 12:
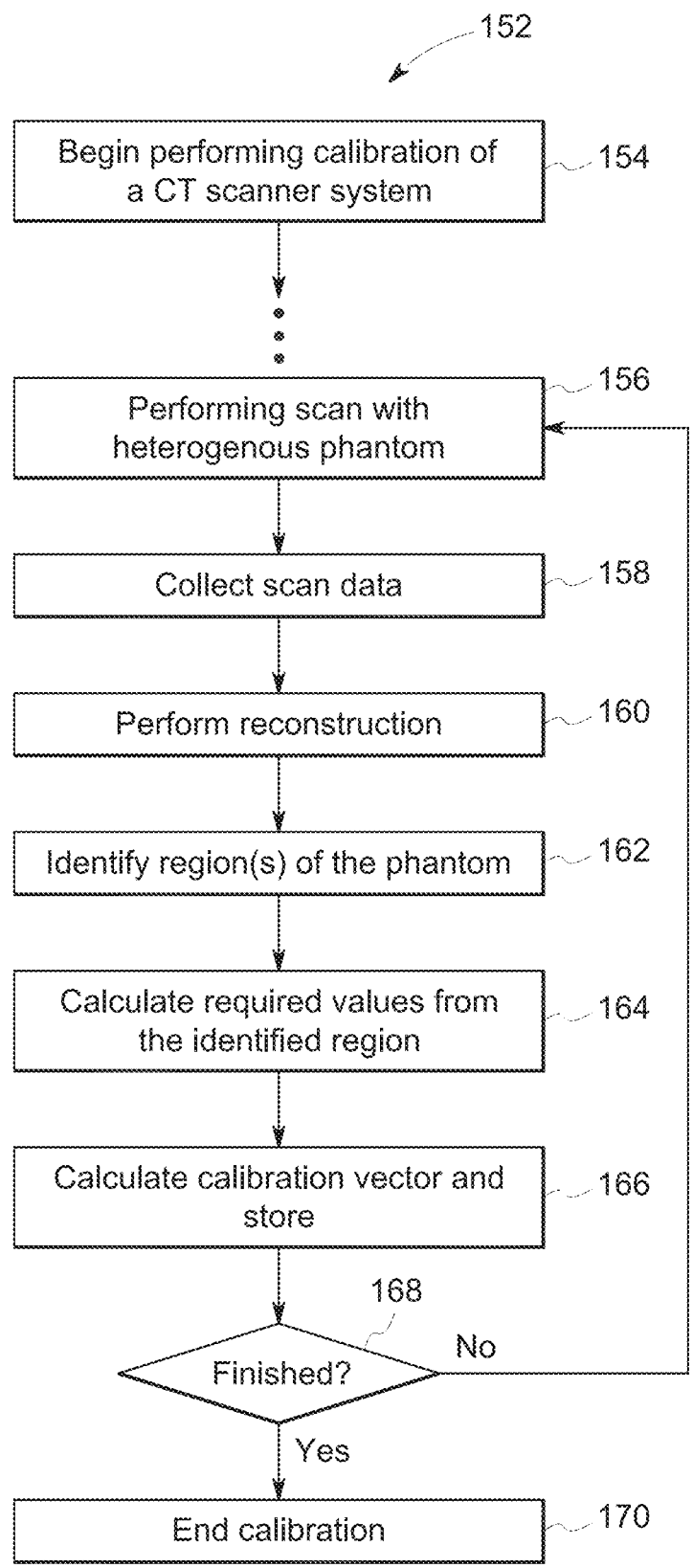
FIG. 12 is a flow chart of a method for performing a calibration process that utilizes a ROI location algorithm, in accordance with aspects of the present disclosure.

As noted above, the ROI location algorithm (e.g., method 66 in FIG. 3) may be utilized in a calibration process. FIG. 12 is a flow chart of a method 152 for performing a calibration process that utilizes the ROI location algorithm. One or more steps of the method 152 may be performed by one or more components (e.g., processing circuitry) of the CT imaging system in FIG. 1 or a device separate or remote from the CT imaging system.

The method 152 includes beginning performing calibration of a CT scanner system (CT imaging system in FIG. 1) (block 154). The method 152 also includes performing a scan of a heterogeneous phantom as described above (block 156). The method 152 further includes collecting or obtaining the scan data (block 158) and performing reconstruction on the scan data to generate a tomographic image of the heterogeneous phantom (block 160). The method 152 still further includes identifying one or more heterogeneous regions within tomographic image of the heterogeneous phantom (block 162). The identification of heterogeneous regions occurs utilizing the ROI location algorithm as described above. The method 152 even further includes calculating the required values (e.g., CT numbers) from the one or more identified heterogeneous regions (block 164). The method 152 yet further includes calculating and storing respective calibration vectors for the one or more heterogeneous regions (block 166). The method 152 includes deciding whether the calibration process is complete (block 168). If not complete, the method 152 returns to block 156. If complete, the method 152 includes ending the calibration process (block 170).

Figure 13:
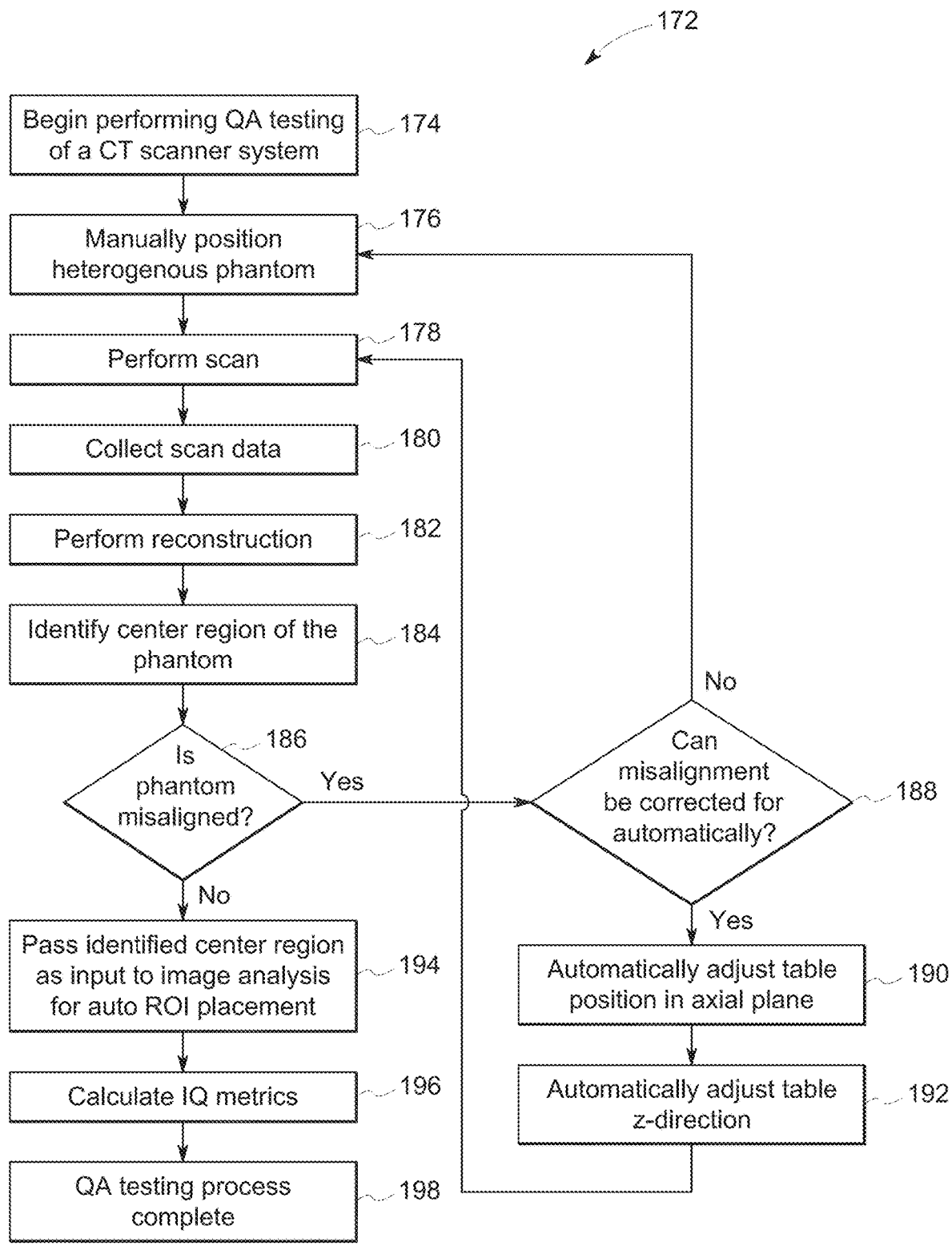
FIG. 13 is a flow chart of a method for performing a QA testing process that utilizes a ROI location algorithm, in accordance with aspects of the present disclosure.

As noted above, the ROI location algorithm (e.g., method 66 in FIG. 3) may be utilized in a QA testing process. FIG. 13 is a flow chart of a method 172 for performing a QA testing process that utilizes the ROI location algorithm. One or more steps of the method 172 may be performed by one or more components (e.g., processing circuitry) of the CT imaging system in FIG. 1 or a device separate or remote from the CT imaging system.

The method 172 includes beginning performing QA testing of a CT scanner system (CT imaging system in FIG. 1) (block 174). The method 172 also includes manually positioning a heterogeneous phantom between the radiation source and the detector of the CT scanner (block 176). The method 172 also includes performing a scan of the heterogeneous phantom (block 178). The method 172 further includes collecting or obtaining the scan data (block 180) and performing reconstruction on the scan data to generate a tomographic image of the heterogeneous phantom (block 182).

The method 172 includes identifying a center region of the heterogeneous phantom (block 184). The method 172 also includes determining if the heterogeneous phantom is grossly misaligned based on the identification of the center region (block 186). If the heterogeneous phantom is grossly misaligned, the method 172 includes determining if the misalignment can be corrected for automatically (block 188). If the misalignment cannot be correctly for automatically, the method 172 returns to block 176. If the misalignment can be corrected for automatically, the method 172 includes automatically adjusting table position (block 190) in axial plane and/or automatically adjusting table location in z-direction (block 192).

If the heterogeneous phantom is not grossly misaligned, the method 172 includes passing the identified center region as input to an image analysis for autonomous ROI placement (e.g., utilizing the ROI location algorithm as described above) (block 194). ROI location algorithm may correct for any minor misalignments (i.e., provide fine tuning). The method 172 also includes calculating image quality (IQ) metrics (block 196). The method 172 further includes ending the QA testing process (block 198).

Technical effects of the disclosed embodiments include providing for deep-learning based autonomous identification of heterogeneous phantom regions (e.g., via region of interest location algorithm). The disclosed embodiments enable the use of a multi-structure in the calibration and QA process without modifying any phantom hardware (e.g., adding a tracer/marker to identify regions). In addition, the deep neural network can be trained with any phantom at any scanning protocols. The ability to automatically identify the regions of interest within the heterogeneous phantom eliminates the need for manual intervention while ensuring the efficacy of the region identification.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method, comprising:
   obtaining, at a processor, a tomographic image of a physical phantom, wherein the physical phantom comprises heterogeneous regions having a plurality of materials with varying attenuation coefficients;
   automatically segmenting, via the processor, the heterogeneous regions from the tomographic image to generate a segmented image;
   automatically identifying, via the processor, a plurality of regions of interest having varying attenuation coefficients within the tomographic image based on the segmented image, wherein the plurality of regions of interest correspond to the heterogenous regions within the physical phantom;
   automatically labeling, via the processor, each region of interest of the plurality of regions of interest as representing a particular material of the plurality of materials; and
   outputting, via the processor, a labeled image of the tomographic image.

2. The computer-implemented method of claim 1, comprising automatically determining, via the processor, an angle of rotation of the physical phantom relative to a properly positioned physical phantom.

3. The computer-implemented method of claim 2, wherein automatically determining the angle of rotation comprises comparing the segmented image to a reference image for a properly positioned physical phantom.

4. The computer-implemented method of claim 2, comprising outputting, via the processor, the angle of rotation of the physical phantom relative to the properly positioned physical phantom.

5. The computer-implemented method of claim 1, comprising outputting, via the processor, a table having both at least a label and the particular material for each region of interest of the plurality of regions of interest.

6. The computer-implemented method of claim 1, wherein each region of interest of the plurality of regions of interests represents a different rod within the physical phantom.

7. The computer-implemented method of claim 1, wherein automatically segmenting the heterogeneous regions from the tomographic image comprises utilizing a trained deep neural network to segment the heterogeneous regions from the tomographic image to generate the segmented image.

8. The computer-implemented method of claim 7, comprising:
   obtaining, via the processor, training data comprising a plurality of image-label pairs, wherein each image-label pair comprises an augmented tomographic image having the heterogeneous regions rotated relative to a properly positioned physical phantom and a corresponding segmentation image of the augmented tomographic image; and
   training, via the processor, a deep neural network utilizing the training data to generate the trained deep neural network.

9. The computer-implemented method of claim 8, comprising generating, via the processor, the training data by performing augmentation on an unaugmented tomographic image, wherein augmentation comprises randomly rotating the heterogeneous regions and adding noise.

10. The computer-implemented method of claim 1, wherein automatically identifying the plurality of regions of interest comprises identifying multi-connectivity pixel regions within the tomographic image and pixel regions greater than a predefined number of connected pixels.

11. The computer-implemented method of claim 1, wherein automatically labeling each region of interest comprises generating a label matrix for the plurality of regions of interest and comparing the label matrix to a static lookup table.

12. The computer-implemented method of claim 1, wherein automatically labeling each region of interest comprises calculating a mean computed tomography number for each region of interest and comparing it to a dynamic lookup table, wherein the dynamic lookup table associates specific computed tomography number ranges with specific materials.

13. The computer-implemented method of claim 1, comprising calculating, via the processor, a respective calibration vector for one or more regions of interest of the plurality of regions of interest based on the labeling of each region of interest.

14. The computer-implemented method of claim 1, comprising calculating, via the processor, image quality metrics based on the labeling of each region of interest as part of a quality assurance test.

15. A computer-implemented method, comprising:
   beginning, via a processor, a calibration of a tomographic imaging system;
   obtaining, via the processor, a tomographic image of a physical phantom utilizing the tomographic imaging system, wherein the physical phantom comprises heterogeneous regions having a plurality of materials with varying attenuation coefficients;
   automatically, via the processor, segmenting the heterogeneous regions from the tomographic image to generate a segmented image;
   automatically, via the processor, identifying a plurality of regions of interest having varying attenuation coefficients within the tomographic image based on the segmented image, wherein the plurality of regions of interest correspond to the heterogenous regions within the physical phantom;

automatically, via the processor, labeling each region of interest of the plurality of regions of interest as representing a particular material of the plurality of materials; and calculating, via the processor, a respective calibration vector for one or more regions of interest of the plurality of regions of interest based on the labeling of each region of interest.

16. The computer implemented method of claim 15, comprising storing, via the processor, the respective calibration vector.

17. The computer-implemented method of claim 15, wherein automatically segmenting the heterogeneous regions from the tomographic image comprises utilizing a trained deep neural network to segment the heterogeneous regions from the tomographic image to generate the segmented image.

18. The computer-implemented method of claim 15, wherein automatically labeling each region of interest comprises calculating a mean computed tomography number for each region of interest.

19. A computer-implemented method, comprising:
beginning, via a processor, quality assurance testing of a tomographic imaging system;
obtaining, via the processor, a tomographic image of a physical phantom utilizing the tomographic imaging system, wherein the physical phantom comprises heterogeneous regions having a plurality of materials with varying attenuation coefficients;
automatically segmenting the heterogeneous regions from the tomographic image to generate a segmented image;
automatically identifying a plurality of regions of interest having varying attenuation coefficients within the tomographic image based on the segmentation image, wherein the plurality of regions of interest correspond to the heterogenous regions within the physical phantom;
automatically labeling each region of interest of the plurality of regions of interest as representing a particular material of the plurality of materials; and
calculating, via the processor, image quality metrics based on the labeling of each region of interest.

20. The computer-implemented method of claim 19, wherein automatically segmenting the heterogeneous regions from the tomographic image comprises utilizing a trained deep neural network to segment the heterogeneous regions from the tomographic image to generate the segmented image.

\* \* \* \* \*